(12) United States Patent
Lawson et al.

(10) Patent No.: US 8,722,031 B2
(45) Date of Patent: May 13, 2014

(54) ANIMAL LITTER DEODORIZING COMPOSITION AND METHOD

(75) Inventors: Frederick Lawson, Somerset, NJ (US); Lauren R. Ciemnolonski, Princeton, NJ (US)

(73) Assignee: Church & Dwight Co., Ltd., Princeton, NJ (US)

( * ) Notice: Subject to any disclaimer, the term of this patent is extended or adjusted under 35 U.S.C. 154(b) by 700 days.

(21) Appl. No.: 12/537,515

(22) Filed: Aug. 7, 2009

(65) Prior Publication Data

US 2011/0033410 A1 Feb. 10, 2011

(51) Int. Cl.
*A61L 9/01* (2006.01)

(52) U.S. Cl.
USPC ........................................ 424/76.6

(58) Field of Classification Search
CPC .................. A61L 9/01; A61L 11/00
See application file for complete search history.

(56) References Cited

U.S. PATENT DOCUMENTS

| | | | |
|---|---|---|---|
| 4,261,849 A * | 4/1981 | Benjaminson | 424/76.6 |
| 4,897,207 A * | 1/1990 | Greene | 252/2 |
| 4,902,434 A | 2/1990 | Dickerson | |
| 5,005,520 A | 4/1991 | Michael | |
| 5,189,987 A * | 3/1993 | Stanislowski et al. | 119/171 |
| 5,290,547 A * | 3/1994 | Bilbrey | 424/76.6 |
| 5,295,456 A | 3/1994 | Lawson | |
| 5,352,444 A | 10/1994 | Cox et al. | |
| 5,421,291 A | 6/1995 | Lawson et al. | |
| 5,735,232 A | 4/1998 | Lang et al. | |
| 5,901,661 A | 5/1999 | Pattengill et al. | |
| 6,015,547 A * | 1/2000 | Yam | 424/49 |
| 6,468,518 B2 * | 10/2002 | Lind et al. | 424/76.6 |
| 6,868,802 B2 | 3/2005 | McPherson et al. | |
| 7,041,279 B1 | 5/2006 | Ali et al. | |
| 7,205,000 B2 | 4/2007 | Einziger | |

OTHER PUBLICATIONS

Kosswig, K. Surfactants. Ullmann's Ecyclopedia of Industrial Chemistry. Wiley-VCH Verlag GmbH & Co. KgaA, pp. 457-458 (published online Jun. 15, 2000; DOI: 10.1002/14356007.a25_747).*
Michael Ash, et al. "Handbook of Preservatives", Synapse Information Resources, Inc. 2004.
Ronald Marks, "Sophisticated Emollients" Thieme 2001. Germany.

* cited by examiner

*Primary Examiner* — Daniel Sullivan
*Assistant Examiner* — Peter Anthopolos
(74) *Attorney, Agent, or Firm* — Fishman & Associates, LLC

(57) ABSTRACT

There is provided an aqueous liquid deodorizing composition for animal lifter and a method of deodorizing animal litter by contacting the litter with the composition by spraying. The composition comprises a crusting inhibitor.

20 Claims, No Drawings

ANIMAL LITTER DEODORIZING COMPOSITION AND METHOD

FIELD OF THE INVENTION

This invention relates to deodorizing compositions and methods of deodorizing animal litter. More specifically it relates to deodorizing compositions for animal litter, wherein the compositions are contacted with the litter by being sprayed onto the litter.

DESCRIPTION OF THE RELATED ART

Presently it is common for pet owners to train their housebroken animals to use absorbing compositions commonly known as litters to urinate and defecate. Pet owners later collect portions of the litter that are saturated with urine and remove feces of their animals. Animal litters usually contain clayey or other absorbent materials. It is beneficial if the litter contains clumping clay. Clumping clays swell after they absorb water-based liquids such as urine and form clumps that are easy to be removed by the pet owner. If a non-clumping clay is the main absorbing ingredient of the litter, then clumping agents or clumping enhancers may be added to the litter to ensure clump formation. The pet owner has to remove the feces and absorbent with the urine quite often in order to prevent emission of unpleasant odors into the surrounding area in their home or apartment. Furthermore, even when the pet owner frequently removes the fecal matter and clumps of absorbent material saturated with urine from the litter, it does not reduce or eliminate odors caused by the remaining uncollected small amounts of absorbent saturated with urine and difficult to collect small pieces of feces.

Animal litters often contain a deodorizing agent. A deodorizing agent that is mixed in with the absorbent material may not be dispersed uniformly in the bag or a box containing the litter or in the litter pan itself and may sink to the bottom. Additional means might be provided to improve the distribution of the deodorizing agent within the litter (see, e.g., U.S. Pat. No. 5,421,291 to Lawson et al.). Various litter additives attempting to eliminate unpleasant odors of animal litter are known. For example, U.S. Pat. No. 5,005,520 to Michael describes a litter additive comprising a perborate and a desiccant, wherein when the waste material comes into contact with the peroxide or peroxygen compound, enough oxygen is produced to oxidize odoriferous compounds into non-odoriferous compounds. U.S. Pat. No. 5,295,456 to Lawson describes a litter additive that includes particles of sodium or potassium bicarbonate coated with mineral oil and agglomerated with expanded perlite. U.S. Pat. No. 6,015,547 to Yam discloses zinc ions solution sprayed onto sodium bicarbonate particles of sufficient size, so that they do not fully dissolve in the aqueous phase. The coated particles are then combined with appropriate absorbent materials of animal litter.

U.S. Pat. No. 7,041,279 to Ali et al. describes an aqueous deodorizing composition comprising an alkali metal tetraborate n-hydrate, a water-soluble/dispersible polymer and a volatile solvent. This composition while acting as urease inhibitor and having bacteriostatic properties creates a film when applied and dried to provide a matrix in which the boron additive, other materials, and animal waste are entrapped.

As the objectionable odors emanating from animal litter continue to remain a problem, an effort has been put into developing deodorizers for animal litters. The deodorizers available on the market can be added to the already purchased animal litter. For example, "Stink Free" brand litter and litter box spray powder deodorizer is a commercial deodorizer that is sprayed in the form of the liquid that later dries to create a solid physical barrier on the bottom of the litter box that prevents the odor contamination of the box and prevents litter from sticking to the box. When applied to the top of dirty litter, it forms a blanket that encapsulates and destroys the odors. A dense layer of powder accumulated on a litter might produce a crust and prevent proper absorption of urine by the absorbent material by allowing for the urine to remain on top of the crust, and therefore inhibit flow of the urine into the absorbent material.

Other available on the market cat litter deodorizers, including, for example, Tidy Cats®, Nil-O-Litter™, and Arm & Hammer® deodorizers, are usually provided in a powder form. They are meant to be added to and mixed with the clumping or non-clumping litter and additionally may be sprinkled on top of it.

These compositions and available products appear to pose several problems. Safety of the animals may be compromised because of the oxygen producing compounds. Additionally, there is the necessity to mix the powdered deodorizers with the litter and a possible lack of uniformity of the distribution of the additive within the litter. Further problems are created by a possibility of crust formation on the surface of the litter, when the deodorizing composition is applied in a liquid form and/or forms a film on the surface of the litter.

SUMMARY OF THE INVENTION

There is provided an aqueous liquid deodorizing composition for animal litter, and a method of deodorizing animal litter by contacting the litter with the composition by spraying. The aqueous composition includes a crusting inhibitor in sufficient quantity to inhibit surface crusting of clumping clay litters but not enough to inhibit the normal clumping properties of the clay.

DETAILED DESCRIPTION OF THE INVENTION

Absorbent materials commonly used in animal litter are clays. It is preferred that the absorbent material clumps when wetted as this allows the pet owner to remove only used portions of the litter, instead of discarding both used and unused portions, which would be wasteful and quite costly. Clumping absorbent material can be water-swellable clays that hydrate and consequently swell in the presence of water or non-water-swellable clays that are provided with an additional clumping agent or clump-enhancing material. This composition preferably comprises water-swellable bentonite clay as a clumping absorbent material. A water-swellable bentonite clay can be selected from the group consisting of sodium bentonite, potassium bentonite, lithium bentonite, magnesium bentonite or their combination. The water-swellable clay contains at least one water-swellable clay mineral. Such mineral can be a montmorillonoid or a smectite. Specific examples include montmorillonite, beidellite, nontronite, hectorite and saponite or their mixtures.

Absorbent material may also include non-clumping or non-water-swellable clays. The non-clumping bentonite clays of the present invention include calcium bentonite, sepiolite, Attapulgite clay, and Fuller's earth. If a non-water-swellable clay is used, then clumping agents or clump enhancing materials may be provided. Such materials include water-swellable clays, polysaccharides, water-soluble gums, dry particulate cellulosic ethers and water-absorbent polymers. Clumping agents and clump enhancing materials promote adhesion of the fine size particles of clay to each other as well as promote adhesion of the granules to form an agglomerate when wetted. Preferably the clumping agent allows the formation of a gelled agglomerate when exposed to a liquid, such as animal urine. Clay particle size suitable for animal litters ranges from about 25 microns to about 3350 microns in diameter.

The preferred bentonite clay of this invention is sodium bentonite. It contains a significant amount of montmorillonite mineral that has the ability to clump and harden after contact with an aqueous liquid such as urine. When contacted with water, the water molecules penetrate between the layers of crystal lattice structure causing interlayer or intra-crystalline swelling and expansion of the entire lattice. This causes the particles of the clayey component of the litter to conglomerate thereby making possible the removal of only that portion of the composition, which is swelled by urine or other aqueous waste liquid.

There is provided an aqueous deodorizing composition and a method of deodorizing animal litter by contacting the litter with the deodorizing composition. The composition comprises a crusting inhibitor, a deodorizing agent, a fragrance, and a fragrance emulsifier. Optionally the composition may further comprise an anti-microbial agent or a fungicide and an odor-blocking agent.

There is also provided a method of deodorizing an animal litter comprising contacting the animal litter with an aqueous composition including a crusting inhibitor, a deodorizing agent, a fragrance, and a fragrance emulsifier. Optionally the composition may further comprise an anti-microbial agent or a fungicide and an odor-blocking agent.

The present composition is provided in a form of an aqueous-based liquid that can be conveniently contacted with the litter, for example, by spraying. While delivering a deodorizing agent and a fragrance to the litter, it helps to prevent a crust formation on the surface of the litter and inducement of clump formation when used on clumping litter. Additionally, clumping of the litter, when clumping results from absorption of animal's urine, would not be affected.

Although it is preferred that the compositions remain free of volatile solvents, it may be useful in some instances to include up to about 5 wt. %, preferably less than 1 wt. % of one or more organic polar solvents including lower $C_2$ to $C_4$ alcohols, $C_2$ to $C_6$ glycols, and alkyl glycol ethers. Many organic liquids interfere with the formation of oriented water layers resulting in reduced water absorbency and clay clumping. For example, non-limiting solvents selected from the group consisting of ethanol, mono-propylene glycol mono-propyl ether, mono-propylene glycol mono-butyl ether di-propylene glycol mono-propyl ether, di-propylene glycol mono-butyl ether, tri-propylene glycol mono-butyl ether, ethylene glycol mono-butyl ether, di-ethylene glycol mono-butyl ether, ethylene glycol mono-hexyl ether and di-ethylene glycol mono-hexyl ether, and mixtures thereof can be used in minimal amounts. "Butyl" includes normal butyl, isobutyl and tertiary butyl groups. The composition will be free of hydrocarbon solvents, including $C_5$ to $C_{16}$ alkane and aromatic solvents that could contribute to respiratory problems for the animals and their owners.

The present composition comprises a water-soluble crusting inhibitor, wherein the crusting inhibitor is dissolved in water. Preferably, a fragrance is emulsified therein. The crusting inhibitors of the present invention are preferably water-soluble electrolytes such as basic metal salts, for example sodium chloride, calcium chloride as well as calcium chloride dehydrate. The composition comprises from about 1 to about 30 wt. % of the crusting inhibitor.

Crusting inhibitors help to prevent crusting of the animal litter upon application of the deodorizing composition to the litter. Crusting on animal litter has been a problem associated with spraying of a deodorizing agent in a liquid form. Crusting occurs when clays present in the litter become poorly aggregated. Crust forms on the clay surface when falling liquid disperses the clay particles causing the dispersed particles to clog the pores immediately beneath the surface. Following drying, the clay surface is "sealed." Urine subsequently deposited onto the litter is more likely to run off than to flow into the litter.

Electrolytes help prevent the crusting of clay particles. Electrolytes increase the degree of crust prevention, which in turn is in direct proportion to the rate of the penetration of water or water-based liquids through clay. Clay particles are built of clay minerals which may consist of two basic crystal structures, tetrahedral sheets of silicon and oxygen and octahedral sheets of magnesium, aluminum and hydroxyl. The basic clay mineral units are formed by stacking these sheet structures with different bonds between them. Owing to broken bonds or isomorphous substitution within clay mineral structures, clay particles develop a net negative charge on the surface. The net negative charge creates a repulsive force between the clay particles, which operates against the van der Wall attractive force present between clay particles. Cations as electrolytes in the clay-pore water system ($Na^+$, $Ca^{++}$, $Mg^{++}$, $K^+$, etc) are attached to the clay particle surface and neutralize some of the negative charges. If the concentration of electrolytes within the system changes, an unbalanced force results which has the potential to change the clay structure. Increases in electrolyte concentration can lead to flocculation of clay structure, volumetric shrinkage and potential to increase hydraulic conductivity, while the decrease in electrolyte concentration has the tendency to disperse clay particles, cause volumetric swelling of clay and potential to decrease the hydraulic conductivity. If higher concentrations of ions are present in the water based formula sprayed onto the clay (e.g., sodium, calcium, magnesium, potassium, ammonium, chloride, sulfate), swelling and crusting are reduced since the ambient water molecules reorient their dipoles towards the added ions and are not properly positioned to form strong bonds within the clay surface.

To counter a decrease in electrolyte concentration, which occurs when an aqueous liquid deodorant solution is applied to a clay surface, the solution can be provided with an electrolyte. The electrolyte helps to reduce the aggregation of clay particles. Electrolytes that are preferable in the composition of this invention are sodium chloride or calcium chloride. Other suitable electrolytes, such as calcium chloride dihydrate or sodium carbonate can also be used. Any water soluble salt containing either sodium, calcium, magnesium, potassium and ammonium cations and/or chloride and sulfate anions can be used.

Another embodiment of this invention includes other crusting inhibitors such as surfactants. Surfactants break the natural surface tension of water overcoming the tendency to form droplets, which causes the dispersion of clay particles and that in turn cause a single grain clay structure, lack of aggregation and surface water repellence. Non-ionic surfactants that can be used with this invention include commercially available surfactants such as Tween® 20, Tween® 40, Tween® 60, Tween® 80, Span®, Incrocas® 30, Incrocas® 35, Incrocas® 40, Acconon® C-10, Acconon® CA-15, Croval® Croval® A-70, Gelucire® 44/14. Gelucire® 50/13, Labrasol®, Solutol® HS15, Volpo® Volpo® 20, Pluronic® F108, Pluronic® F127, Pluronic® F87, Pluronic® L44, Tetronic® 304, Advantage® and their combinations. Other surfactants that can be used include, but are not limited to, non-ionic surfactants such as polyoxyl 40 stearate, polyoxyl 50 stearate, triblock co-polymers of ethylene oxide/propylene oxide/ethylene oxide, sorbitan monopalmitate, sorbitan monostearate, glycerol monostearate, polyoxyethylene stearate, polyoxyethylene 40 sorbitol lanolin derivative, polyoxyethylene 75 sorbitol lanolin derivative, polyoxyethylene 20 sorbitol beeswax derivative, polyoxyethylene 23 lauryl ether, polyoxyethylene 20 cetyl ether, polyoxyethylene 10 stearyl ether, polyoxyethylene 20 stearyl ether, polyoxyethylene oleyl ether, sorbitan monopalmitate, sorbitan monostearate, sorbitan tristearate and their mixtures. Other non-ionic surfactants that may also be used in the present invention include alcohol ethoxylates, alkyl polyglycosides, poly(ethylene oxide-co-propylene oxide) and their combinations. The surfactants that can be used in the present invention include both ionic and non-ionic surfactants. The non-ionic surfactant should not alter electrical conductivity of the water in which it has been dissolved and should migrate evenly through clay. In some embodiments the non-ionic surfactants may be combined with an ionic surfactant. The ionic surfactant usually contains the salt of an organic acid. These are usually sodium salts of either sulfonic or carboxylic acids.

Yet another embodiment of this invention includes polymeric alcohols as crusting inhibitors, acting to stabilize aggregates at the clay surface. Polymeric alcohols that can be used in the composition of this invention include poly (vinyl alcohol) and poly (ethylene) glycol.

The fragrances used in the present composition should possess good odor masking properties while being safe and non-irritating to animals. Examples of fragrances that may be used include commercially available fragrances such as Spa Breeze™ RU-2645 by Takasago Inc., R08-2601 from Robertet Fragrances, Inc., and a fragrance 685942 by Symrise, Inc. Other fragrances may also be used and they may comprise various combinations of the following and other compounds: amyl cinnamic alcohol, amyl cynnamic aldehyde, anisyl alcohol, benzyl alcohol, benzyl benzoate, benzyl cinnamate, benzyl salicylate, citral, citronellol, coumarin, eugenol, geraniol, hexyl cinnamic aldehyde, lilial, limonene, and linallol among others. Fragrances may be present in the composition in the amount of from about 0.1 to about 5.0 wt. %.

The fragrance is typically emulsified in water with a fragrance emulsifier. Emulsifiers reduce the tendency of water insoluble fragrance component to precipitate out of the liquid. The examples of fragrance emulsifiers that can be used with the present invention include Tween® 20 and Tween® 80, otherwise known as Polysorbate 20 and Polysorbate 80, and non-ionic emulsifiers derived from polyoxylated sorbitol and oleic acid. Other suitable emulsifiers include alcohols such as isopropanol, benzyl alcohol, phenoxyethanol, and any high HLB emulsifier including but not limited to highly ethoxylated acids and alcohols. Other suitable emulsifiers may also be used in the composition of the present invention. The emulsifier may be present in the composition in the amount of from about 0.1 to about 5.0 wt. %.

A deodorizer of the present invention may be one or more bicarbonate salts. Suitable bicarbonate salts include sodium bicarbonate, potassium bicarbonate and ammonium bicarbonate and mixtures of one or more bicarbonates. Sodium sesqi-carbonate can also be used. Sodium bicarbonate ($NaHCO_3$) is preferably used as a deodorizer. The deodorizer may be used in the composition in the amount of from about 0.1 to about 5.0 wt. %.

The animal litter deodorizing composition of the present invention may also contain an odor-blocking agent, an antibacterial agent and/or a fungicide. The odor-blocking agent may be one of the ingredients of the fragrance or it may be added to the fragrance. The examples of odor-blocking agents include n-alkyl n-ethyl morpholinium, ethyl sulphates, 4-cyclohexyl-4-methyl-2-pentanone, 4-ethylcyclohexyl methyl ketone, 4-isopropylcyclohexyl methyl ketone, cyclohexyl methyl ketone, 3-methylcyclohexyl methyl ketone, 4-methylcyclohexyl isobutyl ketone, 2,4-dimethylcyclohexyl methyl ketone, 2-cyclohexyl-2-propyl acetate, 2 cyclohexyl-2-propyl propionate, 3-dioxane-4,6-dione, and 1,3-cyclohexadione. Other suitable odor-blocking agents may also be used in the composition. If an odor-blocking agent is used, care has to be taken to ensure that it does not block the desirable odor of the fragrance. Additionally, in order to be an effective odor-blocking agent, the agent normally has to be present at all times. If the odor blocker evaporates before the source of the odor is gone, it is less likely to control the odor.

Antibacterial agents that can be used in the deodorizing composition of the present invention include alkyl quarternary ammonium halides, sodium benzoate, sodium propionate, alkyl ($C_8$-$C_{18}$) dimethyl benzammonium chloride, 4-chloro-3-methylphenol, diallyl ($C_8$-$C_{18}$) dimethylammonium chloride, 2-bromo-2-nitropropane-1-3-diol (Bronopol or Myacide) and salts of undecylenic acid. Fungicides that are applicable in the present invention may include any fungicide that is effective in controlling growth of air-borne fungi that commonly occur in homes, especially basements. Among the effective fungicides are undecylenic acid, alkyl sulfosuccinates, as well as commercially available Busan® 1030, wherein the active ingredient is 2-(thiocyanomethylthio) benzothiazole and Troysan® Polyphase® P-20T wherein the active ingredient is 3-iodo-2-propynyl butyl carbamate. Other suitable anti-bacterial agents and fungicides may also be included in the composition.

In general, the composition can be prepared by mixing the components in water in any order. More typically, the fragrance, since it will likely be less soluble in water, is emulsified in water with a surfactant, and the additional ingredients are then added, including the crusting inhibitor and deodorizer. The following is an example of a composition which may be prepared according to this typical procedure:

EXAMPLE

| % | Ingredient |
|---|---|
| 86.50 | Purified Water |
| 11.00 | Sodium Chloride |
| 1.00 | Sodium Bicarbonate |
| 0.75 | Polysorbate 20 |
| 0.75 | Fragrance |

The animal litter deodorizing composition of the present invention may be delivered to the litter by spraying, for example, from an aerosol spray container or a mechanical trigger spray device.

What is claimed is:
1. An aqueous sprayable deodorizing composition for animal litter consisting essentially of:
a water-soluble electrolyte selected from the group consisting of sodium chloride, calcium chloride, and combinations thereof, wherein the water-soluble electrolyte is at least 11 wt. % to about 30 wt. % of the composition;
a bicarbonate deodorizing agent selected from the group consisting of sodium bicarbonate, potassium bicarbonate, ammonium bicarbonate, sodium sesquicarbonate, and combinations thereof, wherein the bicarbonate deodorizing agent is about 0.1 wt. % to about 5.0 wt. % of the composition;

a fragrance, wherein the fragrance is about 0.1 wt. % to about 5.0 wt. % of the composition, and wherein the fragrance is emulsified in water with an emulsifier, and the emulsifier is about 0.1 wt. % to about 5.0 wt. % of the composition; and wherein the composition is a liquid.

2. The composition of claim 1, wherein the water-soluble electrolyte is sodium chloride.

3. The composition of claim 1, wherein the bicarbonate deodorizing agent is sodium bicarbonate.

4. The composition of claim 2, wherein the bicarbonate deodorizing agent is sodium bicarbonate.

5. The composition of claim 1, wherein the emulsifier is polysorbate 20.

6. The composition of claim 2, wherein the emulsifier is polysorbate 20.

7. The composition of claim 3, wherein the emulsifier is polysorbate 20.

8. The composition of claim 4, wherein the emulsifier is polysorbate 20.

9. The composition of claim 1, wherein the emulsifier is selected from the group consisting of polysorbate 20, polysorbate 80, a non-ionic emulsifier derived from polyoxylated sorbitol and oleic acid, isopropanol, benzyl alcohol, and phenoxyethanol.

10. The composition of claim 1, wherein the fragrance is selected from the group consisting of amyl cinnamic alcohol, amyl cynnamic aldehyde, anisyl alcohol, benzyl alcohol, benzyl benzoate, benzyl cinnamate, benzyl salicylate, citral, citronellol, coumarin, eugenol, geraniol, hexyl cinnamic aldehyde, lilial, limonene, and linalool.

11. The composition of claim 4, wherein the fragrance is selected from the group consisting of amyl cinnamic alcohol, amyl cynnamic aldehyde, anisyl alcohol, benzyl alcohol, benzyl benzoate, benzyl cinnamate, benzyl salicylate, citral, citronellol, coumarin, eugenol, geraniol, hexyl cinnamic aldehyde, lilial, limonene, and linalool.

12. The composition of claim 8, wherein the fragrance is selected from the group consisting of amyl cinnamic alcohol, amyl cynnamic aldehyde, anisyl alcohol, benzyl alcohol, benzyl benzoate, benzyl cinnamate, benzyl salicylate, citral, citronellol, coumarin, eugenol, geraniol, hexyl cinnamic aldehyde, lilial, limonene, and linalool.

13. A method of deodorizing a clay-based animal litter, the method comprising contacting the clay-based animal litter with the composition of claim 1.

14. A method of deodorizing a clay-based animal litter, the method comprising contacting the clay-based animal litter with the composition of claim 4.

15. A method of deodorizing a clay-based animal litter, the method comprising contacting the clay-based animal litter with the composition of claim 8.

16. A method of deodorizing a clay-based animal litter, the method comprising spraying the clay-based animal litter with the composition of claim 1.

17. A method of deodorizing a clay-based animal litter, the method comprising spraying the clay-based animal litter with the composition of claim 4.

18. A method of deodorizing a clay-based animal litter, the method comprising spraying the clay-based animal litter with the composition of claim 8.

19. A method of deodorizing a clay-based animal litter, the method comprising spraying the clay-based animal litter with the composition of claim 11.

20. A method of deodorizing a clay-based animal litter, the method comprising spraying the clay-based animal litter with the composition of claim 12.

* * * * *